United States Patent [19]

Okisaki et al.

[11] Patent Number: 4,822,931

[45] Date of Patent: Apr. 18, 1989

[54] METHOD FOR PREPARATION OF POLYBROMOACENAPHTHENE AND/OR ITS CONDENSATE

[75] Inventors: Fumio Okisaki, Shinnanyo; Masashige Kubo, Tokuyama; Hideo Sakka, Shinnanyo, all of Japan

[73] Assignee: Tosoh Corporation, Shinnanyo, Japan

[21] Appl. No.: 123,533

[22] Filed: Nov. 18, 1987

[30] Foreign Application Priority Data

Nov. 18, 1986 [JP] Japan .............................. 61-272959

[51] Int. Cl.[4] ........................ C07C 17/12; C07C 25/18
[52] U.S. Cl. .................................... 570/208; 570/206; 570/210
[58] Field of Search ........................ 570/206, 208, 210

[56] References Cited

U.S. PATENT DOCUMENTS 3,763,248  10/1973  Mitchell ............................. 570/206
3,833,674  9/1974   Brackenridge ..................... 570/206
3,845,146  10/1974  Moore et al. ....................... 570/206

FOREIGN PATENT DOCUMENTS 005333  2/1974  Japan ................................... 570/210
008307  3/1977  Japan ................................... 570/210

*Primary Examiner*—Werren B. Lone
*Attorney, Agent, or Firm*—Oblon, Fisher, Spivak, McClelland & Maier

[57] ABSTRACT

A method for preparing Con-BAN, in which Con-AN is reacted with bromine in the presence of an iron Lewis acid catalyst and in which the solution of Con-AN and bromine are supplied simultaneously at a given rate into a reactor already containing a halogenated hydrocarbon and an iron catalyst.

6 Claims, No Drawings

METHOD FOR PREPARATION OF POLYBROMOACENAPHTHENE AND/OR ITS CONDENSATE

BACKGROUND OF THE INVENTION

Field of the Invention

The present invention relates to a method for preparation of polybromoacenaphthene and/or its condensate (hereinafter designated as Con-BAN), a useful intermediate of polybromoacenaphthylene and/or its condensate (hereinafter designated as Con-BACN). More particularly, the invention relates to a method for the bromination of an acenaphthene derivative and/or its condensate (hereinafter designated as Con-AN). The structures of Con-AN, Con-BAN, and Con-BACN are shown as follows in formulae (1), (2) and (3), respectively.

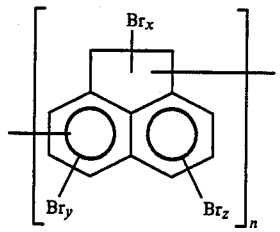

(1)

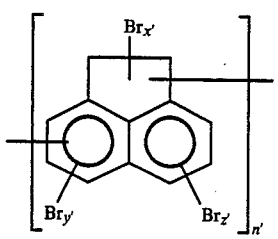

(2)

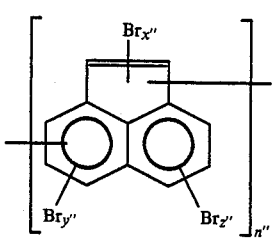

(3)

In formula (1) n is not less than 1; x, y and z are positive values and $x+y+z=0-1$. In formula (2) n' is not less than 1; x', y' and z' are each a positive value ranging from 1-3, and $y'+z'=2-6$. In formula (3) n" is not less than 1; $x''=0-2$, y" and z" are each a positive value ranging from 1-3 and $y''+z''=2-6$.

BACKGROUND OF THE INVENTION

Con-BACN imparts excellent flame retardancy and radiation resistance to high molecular weight substances when mixed in various resins and rubbers. It has been noticed further that the compund will graft polymerize with high molecular weight substances because of the generation of free radicals in the molecule which results from the double bond in the molecule and since the compound is a condensate. Con-BACN therefore exhibits superior compatibility with high molecular weight substances, as well as superior flame retardancy. The radiation resistance of a material containing the condensate can be stably maintained over a long period (Japanese Laid-Open Patent Application No. Sho 56-122862).

It is to be noted that the coating material which is used for electric wire cables, that are utilized in nuclear reactors, breeder reactors and ionic radiation generators, and various resin constituents are required to have radiation resistance as well as flame retardancy. It is expected that Con-BACN will be useful as an additive in materials so utilized.

Con-BACN of the present invention is a compound which contains at least one bromine in an aromatic ring, and formally is a mixture of monomer and condensed product having such a structure as illustrated in formula (3) supra, where polybromoacenaphthene is condensed in a Friedel-Crafts alkylation reaction to produce a polymer mixture having a degree of condensation not less than 2, and then the material is dehydrobrominated. The mode of the bonding between repeating units of the condensate is a single bond between a vinyl carbon and an arylic carbon. The points of bonding are shown in the carbon structural formulas which follow where the degree of condensation is 2.

Bonding between 1 (or 2) and 3'

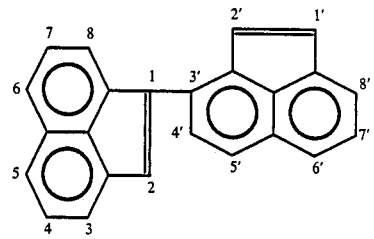

Bonding between 1 (or 2) and 5'

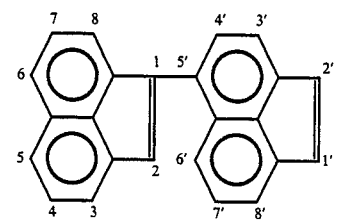

Other points involved in bonding are 1 (or 2)-4', 1 (or 2)-6', 1 (or 2)-7', 1 (or 2)-8'. In the case of a degree of condensation of 3 or more, the number of repeating units increases by any of the above indicated bonding patterns. Con-BACN in the present invention is a compound where the degree of condensation is not more than 10. This mixed material shows excellent compatibility with high molecular weight substances.

Con-BACN can be prepared by dehydrobromination of Con-BAN of formula (2) supra (Japanese Laid-Open Patent Application Nos. Sho 60-139630 and 60-178832).

Con-BAN can be prepared by adding a Lewis acid catalyst to a halogenated hydrocarbon solution of Con-AN (formula (1) supra) and then bromination is carried out by dropping bromine into the solution. hhis method has already been disclosed in Japanese Laid-Open Patent Application No. Sho 59-221313. This method is industrially useful because the reaction solution which is produced that contains Con-AN can be employed without any separation procedures.

Incidentally, the Con-AN employed in the present process can be prepared by the reaction illustrated in scheme (4) below, which has been proposed in Japanese Laid-open Patent Application No. Sho 59-221313. In this method, the side chain of acenaphthene is brominated in a halogenated hydrocarbon solution when subjected to ultraviolet radiation or when in the presence of a radical initiating agent. Subsequently, Friedel-Crafts alkylation is conducted by adding a Lewis acid catalyst to the resultant reaction solution.

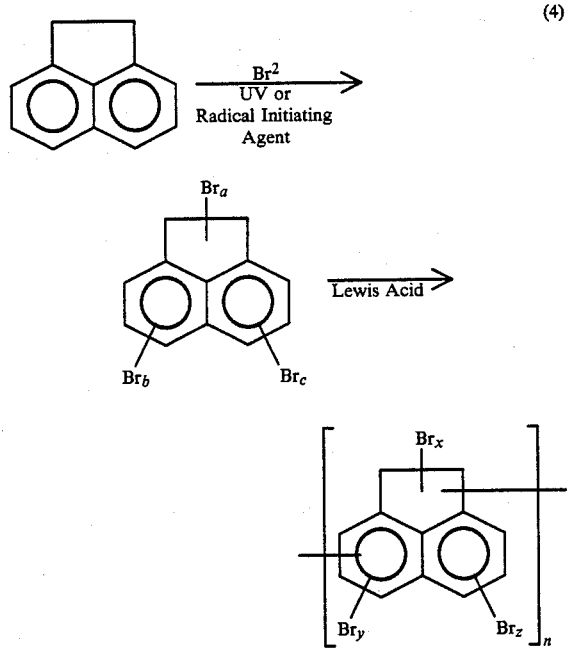

(4)

In the formulas above, x, y, z and n are the same as in formula (1) supra, a is a positive value of 0-2, b and c are each positive values of 0-1, and b+c=0-1.

In the conventional method, however, the condensation occurs as bromination proceeds. It is therefore difficult to control the degrees ff both condensation and bromination. That is, a problem is that under the conditions which increase the degree of bromination, the condensation reaction advances which excessively produce polybromides and/or substances having a high degree of condensation. These substances deposit as insoluble substances from the reaction system because of their low solubility.

The quantity of the insoluble substance thus produced, though depending on reaction conditions, reaches 20 weight percent against the product Con-BACN in the case when Con-BACN is produced which is suitable for ethylene-propylene-diene rubber. In this reaction the yield is about 75 percent, which is far from satisfactory. Furthermore, the insoluble substance has so high a melting point that homogeneous dispersion into high molecular weight substances diminishes. This diminished disperson adversely affects the properties of the material containing the Con-BACN. A need therefore continues to exist for a method of producing Con-BACN which reduces the amount of insoluble substances produced in the reaction where Con-BACN is prepared from Con-BAN and Con-BAN is produced by the bromination of Con-AN.

SUMMARY OF THE INVENTION

Accordingly, one object of the present invention is to provide a method of brominating Con-AN which results in good yields of the desired product Con-BAN while substantially inhibiting the production of insoluble substances.

Briefly, this object and other objects of the present invention as hereinafter will become more readily apparent can be attained by a process in which bromine and a solution of Con-AN are simultaneously introduced at given rates into a reactor already containing a Lewis acid iron catalyst and a halogenated hydrocarbon solvent thereby resulting in a reaction which produces Con-BAN.

DETAILED DESCRIPTION OF THE PREFERRED EMBODIMENTS

When the method of the present invention is practiced, it is possible to obtain Con-BAN which has the same quality as the Con-BAN produced by the conventional method, except it is obtained in higher yields. At the same time the formation of the aforesaid insoluble substances is suppressed. The reason why these beneficial results are realized by the present process is not clear. However, the following may be a reasonable explanation. In this method, the molar ratio of bromine to acenaphthene units can be controlled over the whole period in which these two raw material solutions are mixed by properly determining the feed rate ratios as figured on a mole basis (hereinafter abbreviated as FPR) of bromine to acenaphthene units of Con-AN and the molar ratio of bromine introduced to acenaphthene units (hereinafter abbreviated as the B/A ratio).

Under the FPR and B/A rttio conditions where an excess of bromine to acenaphthene units is present, bromination, especially the rate of bromination of the aromatic ring, relatively increases in the initial stage of the mixing and reaction period. Because the sites which are active to electrophilic attack in the aromatic ring of the acenaphthene units are filled with bromine atoms, the condensation reaction is inhibited and hence the production of insoluble substances and polycondensation are retarded.

Therefore, both the FPR add B/A ratios must be more than given values, preferably the FPR ranging from 5 to 15 and the B/A ratio ranging from 3 to 6. In the case where the FPR ratio is less than 5 or the B/A ratio is less than 3, the promotion of bromination as mentioned above proceeds insufficiently while the condensation occurs. This leads to an increase in the quantity of insoluble substances. Furthermore, in the case where the FPR is more than 15 or the B/A ratio is more than 6, the bromination advances to a great extent and polybromides with lower solubility are deposited, thus increasing the amount of insoluble substances. In the case where the B/A ratio is more than 6, a large excess of bromine remains in the reaction system after completion of the reaction, which results in complicated procedures for the elimination of excess bromine.

The bromination reaction of the present invention is an exothermic reaction. Consequently, it is desired to facilitate the elimination of the heat generated by the reaction. In order to prevent the thermal promotion of the condensation reaction the feed rate of Con-AN should be 1.0 mol or less of acenaphthene units/hr on a reaction scale of 1 mol of acenaphthene units. The feed rate of bromine should be 6.0 mole or less/hr.

The concentration of the Con-AN solution supplied to a reactor should preferably be 1 to 50 weight percent. Concentrations of more than 50 percent Con-AN promote the condensation reaction and further reactions between Con-AN molecules. Concentrations of Con-AN of less than 1 percent are not economical because the quantity of solvent used increases.

The concentration of bromine solution supplied to a reactor should preferably be not less than 50 weight percent. Concentrations less than 50 percent are not economical because much solvent is required. There is no problem when bromine is employed in an undiluted form. Undiluted bromine is particularly desirable from the economic point of view because the quantity of solvent used decreases.

Any solvent which is useful for the preparation of Con-AN solutions and bromine solutions supplied to a reactor can be used if the solvent is inert to the reaction and dissolves the raw materials and products satisfactorily. Preferably halogenated hydrocarbons are employed because of their inertness to the reaction, their ability to dissolve components of the reaction add their availability. No problem occurs in the reaction even when Con-AN and bromine are dissolved in different solvents, but considering the problems involved in recovering mixed solvents, the same solvent should preferably be employed. Suitable solvents include carbon tetrachloride, chloroform, dichloromethane, carbon tetrabromide, bromoform, dibromomethane, 1,2-dichloroethane, 1,1,2-trichloroethane, and the like.

The quantity of halogenated hydrocarbon initially introduced into the reactor should be 0.1 to 1.0 volume relative to the total volume of solvent supplied to the raw material solutions. If less than 1.0 volume is used, the solution in the reaction vessel cannot be adequately stirred during the initial stage of supply of the raw material solutions, and the temperature rises very quickly because of the heat of reaction. Hence, it becomes difficult to control the reaction. On the other hand, a volume ratio of more than 1.0 is undesirable from the economic point of view, because of the increased quantities of solvent which must be employed.

Suitable iron catalysts for the process include Lewis acid iron catalysts such as iron powder, ferrous chloride, ferrous bromide, ferrous iodide, ferrous nitrate, ferrous sulfate, iron sulfide, ferrous oxide, ferric chloride, ferric bromide, ferric iodide, ferrocene, iron phthalocyanine, iron ethylenediaminetetraacetate, preferably ferric chloride. Mixture of two or more of such catalysts can be employed.

The quantity of iron catalyst initially introduced into a reactor should be 0.1 to 5 mol percent per acenaphthene unit. If the quantity is less than 0.1 mol percent, the bromination does not proceed adequately. On the other hand, if the quantity is more than 5 mol percent, the bromination proceeds to a high degree, polybromides with low solubility are deposited, and the resultant insoluble substances increase. Furthermore, the heat stability of the final Con-BACN diminishes, the reason for which remains unclear, and the merchandise value of the product is substantially impaired.

The temperature in the reactor where both Con-AN solution and bromine are supplied should be 0° to 50° C. If the temperature is higher than 50° C., the condensation reaction is promoted and a lot of bromine evaporates. Since the reaction is an exothermic reaction, it is not economical to maintain the temperature below 0° C. When the B/A and FPR ratios are considered, the times at which the Con-AN solution and bromine are supplied do not coincide. Either the Con-AN solution or bromine will be supplied in the latter stage inevitably, preferably the temperature being 0° to 50° C. even at that time. There is no problem if the temperature of the reaction system is raised after completing the supply of the two raw material solutions, preferably resulting promoting the conversion of bromine.

Having generally described this invention, a further understanding can be obtained by reference to certain specific examples which are provided herein for purposes of illustration only and are not intended to be limiting unless otherwise specified.

The production ratio of insoluble substances in the Examples and the Comparative Examples is the quantity of insoluble substance, which is obtained by the following formula (5).

$$\text{Ratio of Insoluble Substances} = \frac{\text{Quantity of Insoluble Substances}}{(\text{Con-}BACN \text{ Yield}) + (\text{Quantity of Insoluble Substances})} \times 100 \quad (5)$$

The average degree of condensation $\overline{DC}$ is calculated by substituting the peak area rate Ai (i is the degree of condensation) for each component indicating a certain degree of condensation by formula (6). The calculation is made after determining the distribution of the degree of condensation by gel permeation chromatography (GPC).

$$DC = \sum_i i \times Ai \quad (6)$$

GPC analysis is carried out under the following conditions.
Column: Tosoh Corporation TSK—Gel G1000H
Detector: Tosoh Corporation Differential Refractometer R1-8
Effluent: Tetrahydrofuran The thermal decomposition rate is expressed as weight percent HBr, which is generated when Con-BACN is heated at 160° C. for 3 hours, against the weight of Con-BACN employed in the experiment.

EXAMPLES 1 TO 7, AND COMPARATIVE EXAMPLES 1 AND 2

Con-AN solutions employed in Examples 1 to 7 and Comparative Examples 1 and 2 are prepared according to the following procedure. Acenaphthene (77.1 g–0.500 mol) and 1.64 g of $\alpha,\alpha'$-azobisisobutyronitrile (10 mmol) were dissolved in 351 g of carbon tetrachloride in a four necked 1-liter flask under a dry nitrogen atmosphere, to which a solution, in which 52.0 g (0.375 mol) of bromine is dissolved in 237 g (the concentration of bromine is 18 wt %) of carbon tetrachloride, is dropped in 50 min with stirring and refluxing, and then refluxing is continued for a further 30 min. After cooling to room temperature, a solution of titanium tetrachloride 4.74 g (25 mmol) dissolved in carbon tetrachloride 42.7 g is added to the solution in 10 min and is further stirred at room temperature for one hr. A reaction solution is obtained which contains 81.1 g of Con-AN and a $\overline{DC}$ of 2.30. The bromine content is 5.6%, (weight concentration 11%, acenaphthene unit 0.500 mol).

Bromination of Con-AN is carried out with an amount of reaction solution which corresponds to 0.5 mol of acenaphthene thus obtained, by to the following method: A 200 g amount of carbon tetrachloride is introduced into a four necked 1-liter flask and ferric chloride is added as a catalyst in the quantities shown in Table 1. The Con-AN solution and bromine are supplied simultaneously with vigorous stirring at the temperatures shown in Table 1. Con-AN is supplied in an amount which provides 0.14 mol-acenaphthene unit/hr. Bromine is added undiluted at the feed rate determined from the FPR and B/A ratios shown in Table 1. In Examples 1 to 7 and Comparative Examples 1 and 2, even after the supply of bromine is completed, Con-AN is supplied sequentially. After completing the supply of Con-AN, stirring is continued at the same temperature for 0.5 hr. The solution is then heat aged at reflux for the periods shown in Table 1. The reaction solution, after removing insoluble substances by filtration, was washed with water. Thereafter, unreacted bromine is reduced by treatment with a solution of sodium hydrogen sulfite (25 wt %) and then further washed thereby obtaining a carbon tetrachloride solution of Con-BAN. Incidentally, the insoluble substances are washed out with carbon tetrachloride, and after separation, are dried at 120° C. for 8 hr, and the rate of production of insoluble matter is calculated. The results obtained are summarized in Table 1.

Subsequently, the Con-BAN solution is refluxed with a potassium hydride solution containing 56.1 g of potassium hydride (1.00 mol) dissolved in 215 ml of methanol for 2 hours, and then the resultant solution is washed with water, with 5% of sulfuric acid and then with water. A carbon tetrachloride solution of Con-BACN is obtained.

To the Con-BACN solution is added 0.29 g of polyoxyethylene (20) sorbitan monopalmitate (Wako Pure Chemical Industries, Ltd.) as a surface active agent, and this solution is dropped into 1.5 liter of water in which 0.14 g of the surface active agent is dissolved and heated at 95° C. for 3 hr. By this treatment carbon tetrachloride in the Con-BAN solution is eliminated as it is azeotropically distilled with water. The precipitated Con-BACN powder is filtered and dried under normal pressure at 120° C. for 8 hr. The yield, yield percent, bromine content, and heat decomposition rate of the powder are all summarized in Table 2.

COMPARATIVE EXAMPLE 3

Into a Con-AN solution (acenaphthene unit 0.500 mol) obtained by the same procedure as that in Examples 1 to 7, 384 g of bromine (2.40 mol) is dropped at 30° C. in 3.5 hr. Stirring is continued for 0.5 hr at the same temperature, and is further heated for 6 hr at reflux. This reaction mixture is treated by the same method as that in Examples 1 to 7. The results are shown in Tables 1 and 2.

TABLE 1

| | B/A Ratio | FPR | Catalyst (mol %) | Reaction Solution Temperature (°C.) | Reflux Maturation (hr) | Insoluble Substance (wt %) |
| --- | --- | --- | --- | --- | --- | --- |
| Example 1 | 4.8 | 10 | 1 | 30 | 6 | 3.40 |
| Example 2 | 4.8 | 7.5 | 3 | 30 | 6 | 4.40 |
| Example 3 | 4.8 | 10 | 3 | 30 | 6 | 5.05 |
| Example 4 | 4.8 | 15 | 3 | 30 | 5 | 5.79 |
| Example 5 | 4.6 | 10 | 1 | 30 | 6 | 3.15 |
| Example 6 | 5.0 | 10 | 1 | 30 | 6 | 5.53 |
| Example 7 | 4.8 | 10 | 1 | 50 | 6 | 4.00 |
| Comparative Example 1 | 4.8 | 20 | 3 | 30 | 5 | 12.19 |
| Comparative Example 2 | 4.8 | 10 | 1 | 60 | 6 | 10.21 |
| Comparative Example 3 | 4.8 | 0 | 5 | 30 | 6 | 19.50 |

TABLE 2

| | Yield (g) | Yield (%) | DC | Bromine Content (wt %) | Pyrolysis Rate (wt %) |
| --- | --- | --- | --- | --- | --- |
| Example 1 | 180.59 | 89.5 | 2.43 | 63.2 | 0.03 |
| Example 2 | 176.43 | 85.0 | 2.47 | 64.0 | 0.04 |
| Example 3 | 182.13 | 85.1 | 2.44 | 64.2 | 0.06 |
| Example 4 | 187.48 | 85.3 | 2.30 | 64.5 | 0.09 |
| Example 5 | 171.82 | 89.6 | 2.40 | 61.3 | 0.04 |
| Example 6 | 179.70 | 88.3 | 2.43 | 63.5 | 0.04 |
| Example 7 | 179.32 | 88.3 | 2.48 | 63.4 | 0.03 |
| Comparative Example 1 | 187.72 | 79.1 | 2.30 | 67.0 | 0.18 |
| Comparative Example 2 | 177.78 | 79.8 | 2.54 | 63.3 | 0.04 |
| Comparative Example 3 | 153.20 | 75.9 | 2.43 | 63.2 | 0.08 |

It is clear from the results of the Examples and the Comparative Examples that the method of the present invention is useful for the preparation of Con-BACN having the same quality as the Con-BACN product prepared by the conventional method. The formation of insoluble substances is suppressed quite substantially in the production of Con-BAN from Con-AN. Thus, the total yield of Con-BACN produced from acenaphthene is enhanced.

Having now fully described the invention, it will be apparent to one of ordinary skill in the art that many changes and modifications can be made thereto without departing from the spirit or scope of the invention as set forth herein.

What is claimed as new and desired to be secured by patents of the United States is:

1. A method for preparing polybromoacenaphthene, condensates thereof, or mixtures thereof, each represented by the formula:

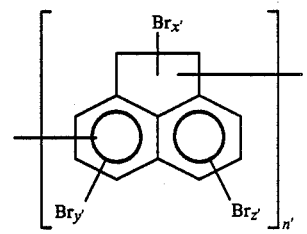

wherein n' is not less than 1, x', y' and z' are each a positive value ranging from 1–3; and y'+z' is a value ranging from 2 to 6, which comprises:

placing an iron catalyst and a halogenated hydrocarbon solvent in a reactor;

simultaneously adding a solution of an acenaphthene derivative, a condensate thereof or mixtures thereof, each represented by the formula:

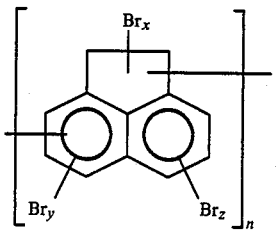

wherein n is not less than 1; x, y and z are each a positive value and x+y+z is zero or one, and bromine to said reactor such that the feed ratio, on a mole basis, of bromine to acenaphthene units of the acenaphthene derivative, its condensates or mixtures thereof is 5 to 15 and such that the molar ratio of bromine introduced into the reactor relative to the acenaphthene units of the acenaphthene derivative, condensates thereof or mixtures thereof is 3 to 6; and reacting the materials added to said reactor at a temperature ranging from 0° to 50° C.

2. The method of claim 1, wherein the iron catalyst is ferrous chloride.

3. The method according to claim 1, wherein the amount of the iron catalyst is 0.1 to 5 mol % with respect to the acenaphthene units of the acenaphthene derivative, condensates thereof or mixtures thereof.

4. The method of claim 1, wherein said halogenated hydrocarbon solvent is carbon tetrachloride, chloroform, dichloromethane, carbon tetrabromide, bromoform, dibromomethane, 1,2-dichloroethane or 1,1,2-trichloroethane.

5. The method of claim 1, wherein said iron catalyst is iron power, ferrous chloride, ferrous bromide, ferrous iodide, ferrous nitrate, ferrous sulfate, iron sulfide, ferrous oxide, ferric chloride, ferric bromide, ferric iodide, ferrocene, iron phthalocyanine or iron ethylenediaminetetraacetate.

6. The method of claim 1, wherein the volume of solvent in the reactor initially ranges from 0.1 to 10 volume relative to the total volume of solvent in the raw material solutions.

* * * * *